United States Patent [19]

Weiss et al.

[11] 4,139,713
[45] Feb. 13, 1979

[54] STEROIDAL INTERMEDIATES FROM THE CONDENSATION PRODUCT OF DIMETHYL-3-KETOGLUTARATE AND GLYOXAL

[75] Inventors: Ulrich Weiss, Bethesda; Kenner C. Rice, Rockville, both of Md.

[73] Assignee: The United States of America as represented by the Secretary of the Department of Health, Education and Welfare, Washington, D.C.

[21] Appl. No.: 817,051

[22] Filed: Jul. 19, 1977

Related U.S. Application Data

[62] Division of Ser. No. 690,361, May 26, 1976, Pat. No. 4,069,241.

[51] Int. Cl.² ............................................. C07C 69/95
[52] U.S. Cl. .................................... 560/116; 560/119
[58] Field of Search ........................................ 560/116

[56] References Cited

PUBLICATIONS

Rice et al., Tetrahedron Letters 44, pp. 3767–3770, (Oct. 1975).
Weiss et al., Tetrahedron Letters 47, pp. 4885–4887, (1968).
Edwards et al., J. Org. Chem. 38, p. 2919 (1973).
Rice et al., Tetrahedron Letters 44, (Oct. 1975).

Primary Examiner—Jane S. Myers
Attorney, Agent, or Firm—John S. Roberts, Jr.; Norman J. Latker; Thomas G. Ferris

[57] ABSTRACT

Tricyclic aromatic compounds of the formula

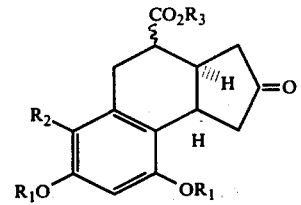

including those wherein:
(a) $R_1$ is H, $R_2$ is carbomethoxy, and $R_3$ is methyl;
(b) $R_1$ is acetyl, $R_2$ is carbomethoxy, and $R_3$ is methyl;
(c) $R_1$ and $R_3$ are methyl and $R_2$ is carbomethoxy;
(d) $R_1$, $R_2$, and $R_3$ are hydrogen; and
(e) $R_1$ and $R_3$ are methyl and $R_2$ is hydrogen are intermediates for the total synthesis of steroids.

1 Claim, No Drawings

STEROIDAL INTERMEDIATES FROM THE CONDENSATION PRODUCT OF DIMETHYL-3-KETOGLUTARATE AND GLYOXAL

This is a division of application Ser. No. 690,361, filed May 26, 1976, now U.S. Pat. No. 4,069,241.

BACKGROUND OF THE INVENTION

This invention relates to novel tricyclic aromatic compounds which correspond to the B, C, and D ring skeleton of steroids and which can be used as intermediates for the total synthesis of steroids.

Reported synthesis of the B, C, and D ring skeleton of steroids include those of Joly et al (U.S. Pat. No. 3,274,233) by reaction between a 2-cyano-2-lower alkyl-6-methoxytetralone-1 and a di(lower alkyl)succinate to produce a lower alkyl ester of 1-oxo-8-lower alkyl-4,5-(4'-methoxybenzo)-$\Delta^{3(9)}$-hydrindene-3-carboxylic acid

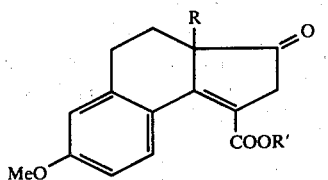

A synthesis reported by Nominé et al (U.S. Pat. No. 3,115,507) requires conversion of 6-methoxy-3,4-dihydronaphthyl-(2,1)-isoxazole by reaction with an alkyl halide to a 2-alkyl-2-cyano-6-methoxytetralone-1 which is condensed with a dialkyl succinate to give 5-methoxy-13$\beta$-substituted-15-alkoxycarbonyl-$\Delta^{5,7,9,14}$-des-A-gonatetraene-17-one

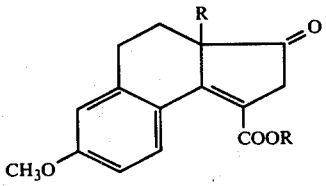

It is apparent from the foregoing that there is a continuing need for routes to the B, C, and D ring skeleton of steroids which are convenient, which use commercially available inexpensive starting materials and which give high yields of tricyclic aromatic steroid intermediates. Also, in view of depletion of natural sources of intermediates for the total synthesis of steroid drugs, the development of totally synthetic routes is of increasing importance.

Condensation of glyoxal with dimethyl 3-ketoglutarate in aqueous solution buffered to pH 6.0 to a hexacarbomethoxy compound

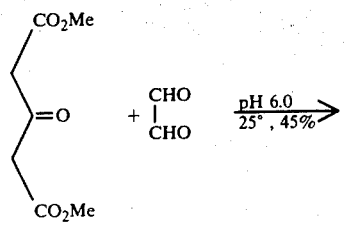

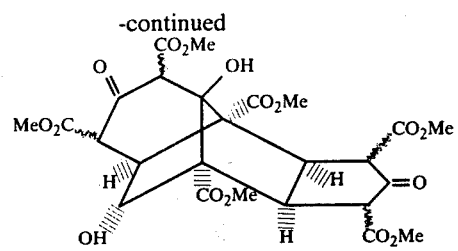

and conversion to a tetracyclic aldol was reported by K. C. Rice et al, *Tetrahedron Letters*, No. 44, 3767 (1975).

It has been found, in accordance with this invention, that a series of reactions, starting from the foregoing hexacarboalkoxy compound, are extremely simple and convenient, requiring no chromatographic separation steps and provide valuable B, C, D ring precursors of steroidal estrogens and antifertility drugs.

SUMMARY OF THE INVENTION

In a compositional aspect, this invention relates to novel tetrahydrocyclopentano[a]naphthalene compounds of Formula I:

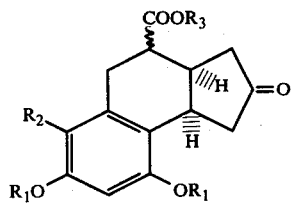

wherein $R_1$ is H, acetoxy or methyl;
$R_2$ is hydrogen or carbomethoxy; and
$R_3$ is hydrogen or methyl.

In a preparative aspect, this invention relates to a method of preparing a tricyclic aromatic compound of Formula Ia:

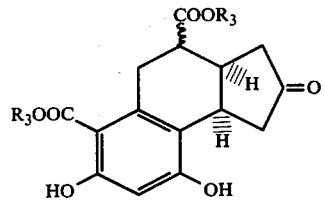

by the steps of: (a) condensing three moles of a dialkyl 3-ketoglutarate of the formula $R_3OOCCH_2COCH_2COOR_3$ with two moles of glyoxal to produce a hexacarbomethoxy compound of Formula II:

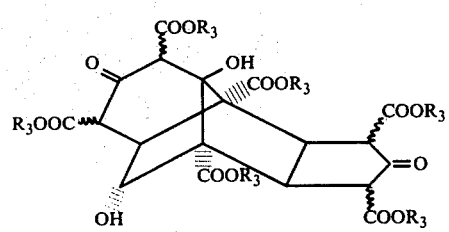

(b) hydrolyzing the hexacarbomethoxy compound to a dicarbomethoxyaldol of Formula III:

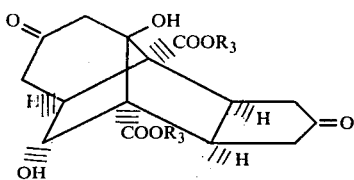

(c) acetylating the dicarbomethoxyaldol to an acetoxy compound of Formula IV:

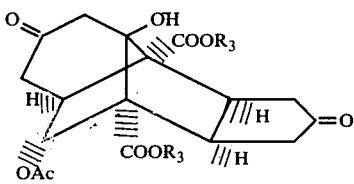

wherein Ac is $CH_3CO$;

(d) thermolyzing the acetoxy compound to a tricyclic compound of Formula V:

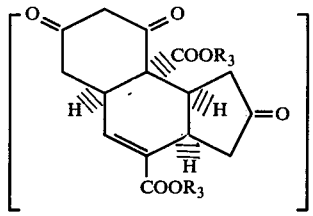

which spontaneously aldolizes to an intramolecular aldol of Formula VI:

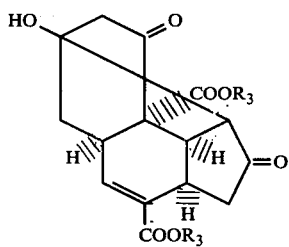

and treating the intramolecular aldol with alkali metal methoxide to form the tricyclic aromatic compound of Formula Ia, wherein $R_3$ and Ac are as above; or treating said acetoxy compound with the alkali metal methoxide to form said tricyclic aromatic compound of Formula I, wherein $R_3$ is as above;

(e) and converting compound Ia to other compounds of Formula I by etherification, saponification, esterification and/or decarboxylation.

In another compositional aspect, this invention relates to novel hexacarbomethoxy compounds, which are intermediates for the total synthesis of steroids, of Formula II.

DETAILED DESCRIPTION

In compounds of Formula I, $R_1$ is H, acetyl, or methyl.

$R_2$ is hydrogen or carbomethoxy.

$R_3$ is hydrogen or methyl.

Compounds of Formula I which are especially preferred are:

(a) $R_1$ is H;
(b) $R_1$ is acetyl;
(c) $R_1$ is methyl;
(d) $R_2$ is H, including (a)-(c);
(e) $R_2$ is carbomethoxy, including (a)-(c);
(f) $R_3$ is H, including (a)-(e);
(g) $R_3$ is methyl, including (a)-(e);
(h) $R_1$ is H, $R_2$ is carbomethoxy, and $R_3$ is methyl;
(i) $R_1$ is acetyl, $R_2$ is carbomethoxy, and $R_3$ is methyl;
(j) $R_1$ and $R_3$ are methyl and $R_2$ is carbomethoxy;
(k) $R_1$, $R_2$, and $R_3$ are H; and
(l) $R_1$ and $R_3$ are methyl and $R_2$ is H.

A particularly preferred compound of Formula I ($R_1$ is H, $R_2$ is COOMe and $R_3$ is Me) corresponds to the following structure, using steroid numbering:

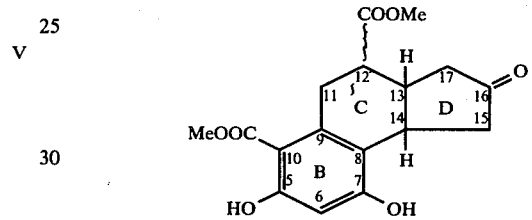

According to IUPAC rules of organic nomenclature and Chemical Abstracts practice, compounds of Formula I are derivatives of 1H-benz[e]indene:

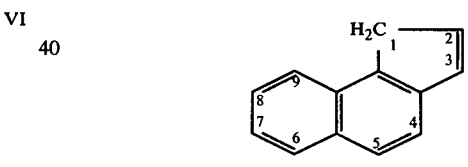

and the above compound of Formula I is named dimethyl 2,3,3aα,4,5,9b α-hexahydro-7,9-dihydroxy-2-oxo-1H-benz[e]indene-4,6-dicarboxylate.

The tetracyclic dicarboalkoxy aldol of Formula III is obtained by partial acid hydrolysis of the corresponding hexacarboalkoxy compound of Formula II, which itself is formed in 45% yield by simply stirring a solution of alkyl 3-ketoglutarate and glyoxal at room temperature in aqueous solution buffered to pH 6.0 [K. C. Rice et al, *Tetrahedron Letters*, No. 44, 3767 (1975)]. (Lib. recd. date, P.O., Nov. 11, 1975)

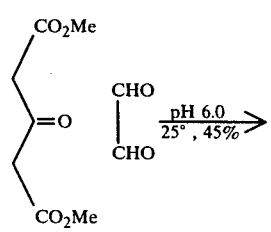

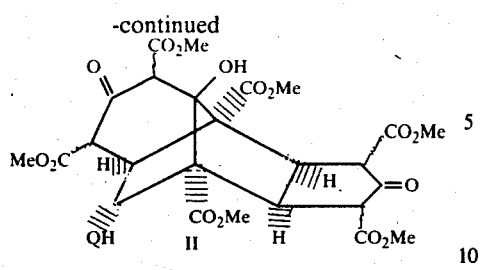

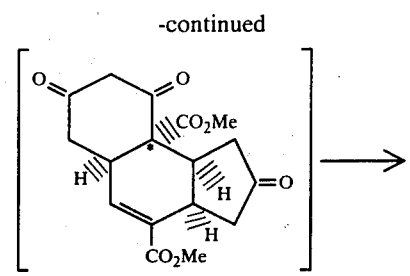

V (R$_3$ is Me)

Pyrolysis of an acetoxy compound of Formula IV, the monoacetate of a compound of Formula III, was shown to give an intramolecular aldol of Formula VI, thought to arise from intramolecular aldolization of a primary tricyclic thermolysis product of Formula V.

III (R$_3$ is Me)

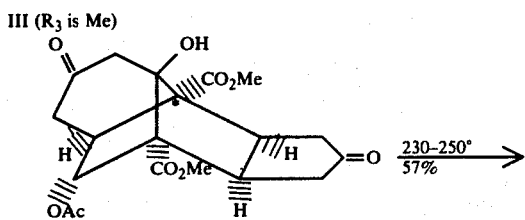

IV (Ac is acetyl, R$_3$ is Me)

VI (R$_3$ is Me)

Action of sodium methoxide (10 equivalents) in refluxing methanol on either IV (R$_3$ is Me, Ac is acetyl) or VI (R$_3$ is Me) converted each compound in about 60% yield to a compound of Formula I (R$_1$ is H, R$_2$ is COOMe, R$_3$ is Me), which formed a diacetate (I; R$_1$ is acetyl, R$_2$ is COOMe, R$_3$ is Me) and a dimethyl ether (I; R$_1$ and R$_3$ are Me, R$_2$ is COOMe). The formation of these two derivatives, a singlet, 1H, at δ 6.38 in the nmr spectrum if I (R$_1$ is H, R$_2$ is COOMe, R$_3$ is Me) and other data suggest a diphenolic structure with a single free position on the aromatic ring.

Conversion of compounds of Formulas IV, V, or VI to a benzenoid compound isomeric with VI can obviously take place only if the quaternary nature of the carbon marked by an asterisk is altered. Two possibilities for such a change can be formulated for cases in which R$_3$ is Me (See Scheme I).

Scheme I

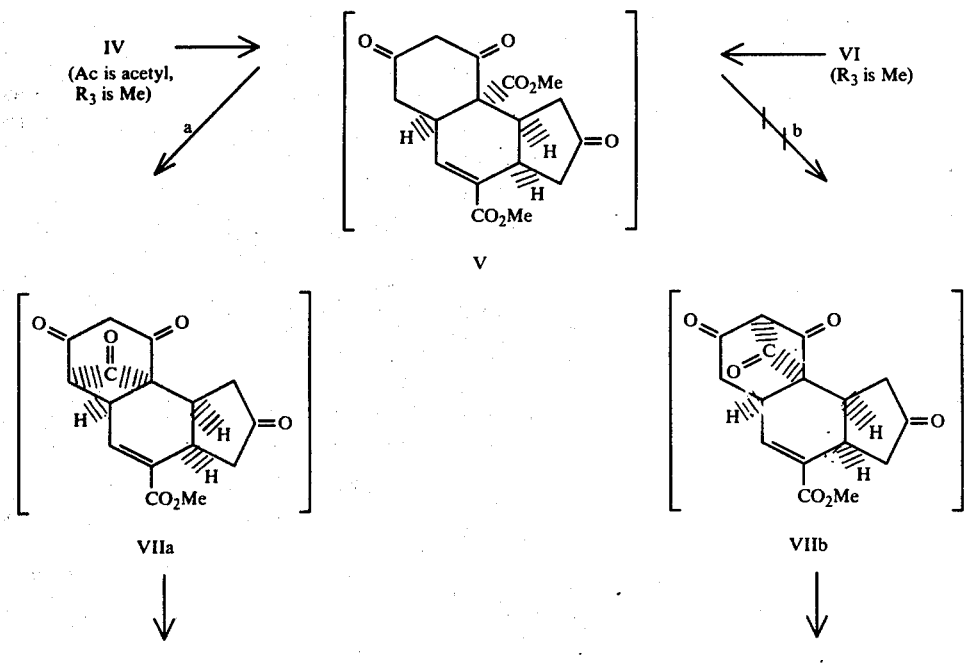

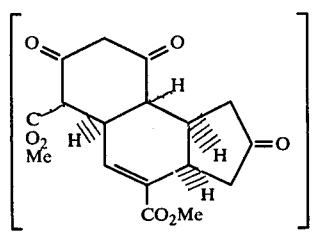

VIIIa

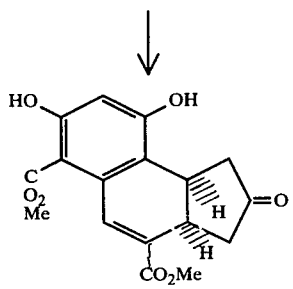

I

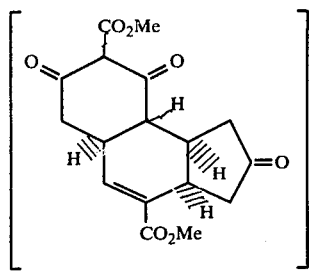

VIIIb

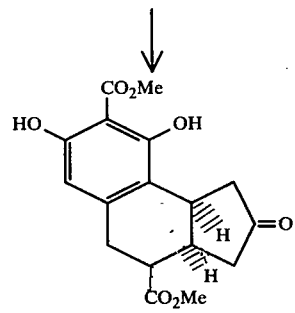

IX

In both cases, dealdolization of VI to V by NaOMe is assumed. Internal, base-promoted acrylation of V can next produce two different cyclobutanone intermediates, VIIa or b. The four-membered rings in these intermediates would then undergo cleavage as indicated, to give VIIIa or b, respectively. Their conversion to the aromatic structures, I and IX, by enolization, extraction of the doubly allylic proton at the ring juncture by the base, and shift of the double bond into the ring is thought to be unexceptional; the aromaticity of the resulting structure provides a powerful driving force.

Except for the $^1$H nmr spectrum, the spectroscopic properties of the aromatic compound are compatible with either structure I or IX. Decision in favor of the former is based on the presence, in the proton nmr spectrum, of two signals from the phenolic hydroxyls ($D_2O$-exchangeable singlets, 1H each) with widely different chemical shifts; δ 6.79 and 11.60, respectively. These δ-values prove that only one of the two hydroxyls, the one giving rise to the signal at δ 11.60, is adjacent to the aromatic carbomethoxy group and hydrogen-bonded to it. This situation prevails in I, while both hydroxyls in IX would be bonded, and should produce coinciding or closely adjacent signals at much lower field than δ 6.79. The findings on model compounds prove the correctness of this interpretation: methyl 2,6-dihydroxybenzoate, δ 9.78 ($D_2O$ exchangeable singlet, 2H); methyl 2,4-dihydroxybenzoate, δ 6.55 and 11.28 ($D_2O$-exchangeable singlets, 1H each).

Structure I of the compound is further confirmed by the fact that the signals from the four oxygen-bound methyl groups of its dimethyl ether (two aromatic methoxyls, two carbomethoxy groups) show marked upfield shifts upon addition of benzene to the solution of the compound in $DCCl_3$. It is well established that significant (> 0.1 δ) upfield shifts of signals from methoxyls on aromatic rings occur on addition of benzene, provided at least one position ortho to the methoxyl is unsubstituted [H. M. Fales and K. S. Warren, *J. Org. Chem.*, 32, 501 (1967)]. This is the case in I but not IX.

The free acid ($R_3$ is H) corresponding to I should lose $CO_2$ with great ease to give the corresponding resorcinol (I; $R_1$, $R_2$, and $R_3$ are H), readily recognizable as such by the characteristic nmr signals for two aromatic protons in meta-relationship. Saponification of the ester (I; $R_1$ is H, $R_2$ is COOMe, $R_3$ is Me) with aqueous sodium hydroxide, followed by acidification of the warm solution with hydrochloric acid, gave the resorcinol (I; $R_1$, $R_2$, $R_3$ are H) directly. The compound showed the expected AB system, with the signals centered at δ 6.18 and 6.30; J = 2.3 Hz. Treatment of the resorcinol with dimethyl sulfate and $K_2CO_3$ in acetone gave the diether (I; $R_1$ and $R_3$ are Me, $R_2$ is H).

Compounds of Formula I are intermediates for total synthesis of steroids, particularly, but not only, steroidal estrogens or antifertility drugs which lack the methyl group 19 at C-10 of the steroid nucleus. Introduction of the methyl group 18 at C-13, construction of ring A of the steroid nucleus, and other transformations of compounds of Formula I will give access to active compounds including prednisone, medroxyprogesterone, mestranol, and ethinylestradiol.

In the total synthesis of steroids from compounds of Formula I, the optically inactive products obtained must be separated into optically active antipodes, preferably at an early stage of the synthesis. It is expected that in the synthesis of compounds of this invention, the compounds of Formula II can be separated into optical isomers by reaction of the secondary hydroxyl group with an optically active acid and resolution of the ester.

Although the C/D ring junction is cis, this can be converted to the normal trans-steroidal structure.

It is thought that compounds of Formula II are formed by way of 2,4,6,8-tetracarboalkoxybicyclo[3.3.-0]octane 3,7-dione from 2 moles of dialkyl 3-ketoglutarate and 1 mole of glyoxal. Further reaction with dialkyl 3-ketoglutarate and glyoxal yields compounds of Formula II.

Exposure of compounds of Formula II to alkali is expected to form the achiral 2,4,6,8-tetracarboalkoxybicyclo[3.3.0]octane 3,7-dione of the structure:

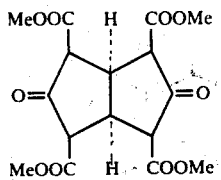

which can be reconverted to the racemic bicyclo compound at pH 6.0. Isolation of optically pure isomers can follow.

Alternatively, optically active compounds of Formula II can be formed by conducting condensation of the 3-ketoglutarate and glyoxal in the presence of an optically active agent, e.g., an optically active acid or base in the buffer mixture.

Elaboration of the A ring to produce estrogens or antifertility drugs can be done by conventional methods.

Without further elaboration, it is believed that one skilled in the art can, using the proceding description, utilize the present invention to its fullest extent. The following preferred specific embodiments are, therefore, to be construed as merely illustrative and not limitative of the remainder of the disclosure in any way whatsoever.

Satisfactory elemental analyses were obtained for all new compounds. Melting points are uncorrected and were taken on a Kofler hot stage. Mass spectra of all new compounds were determined using a Hitachi Perkin-Elmer RMU-6E spectrometer; they showed the expected molecular ions ($M^+$). The $^1H$ and $^{13}C$ nmr spectra (TMS internal reference), which were determined for all new compounds, were consistent with the structures assigned. The $^1H$ spectra were recorded using Varian HR-220 instrument; the $^{13}C$ spectra were determined using a Varian XL-100 spectrometer equipped with a Digilab Fourier transform accessory.

EXAMPLE 1

Reaction of acetoxy compound (IV; $R_3$ is Me and $R_1$ is Ac) with NaOMe. Preparation of I ($R_1$ is H, $R_2$ is COOMe, $R_3$ is Me).

To a solution of Na (6.9 g 300 mmole) in MeOH (450 ml) was added IV ($R_3$ is Me) (12.0 g, 30 mmole). The solution was heated under reflux for 3 hours under nitrogen, cooled, acidified with HCl gas, and filtered. The filtrate was evaporated in vacuo. The residue was dissolved in hot dioxane (200 ml), treated with decolorizing charcoal, filtered, and evaporated. The residue was crystallized from MeOH—H$_2$O (90:10) to give I ($R_1$ is H, $R_2$ is COOMe, $R_3$ is Me) (6.4 g, 64%), mp 206°–9°. Recrystallizaton from 95% EtOH gave pure material, mp 210°–12°, $M^{30}$ = 394; ir (KBr), 3370, 1730, 1650 and 1600 cm$^{-1}$; uv $\lambda_{max}^{EtOH}$ = 304 ($\epsilon$ = 5100), 263 ($\epsilon$ = 10,300) 215 nm ($\epsilon$ = 16,600); nmr (DCCl$_3$) $\delta$ 1.92–2.12 (m, 1H), 2.27–2.84 (m, 4H), 3.01–3.23 (m, 2H), 3,42–3.56 (m, 1H), 3.57–3.74 (m, 1H), 3.78 (s, 3H, OC$\underline{H}_3$), 3.95 (s, 3H, OC$\underline{H}_3$), 6.38 (s, 1H, Ar$\underline{H}$), 6.79 (s, 1H, exchanges with D$_2$O, O$\underline{H}$) and 11.60 (s, 1H, exchanges with D$_2$O, O$\underline{H}$).

EXAMPLE 2

Diacetate of I ($R_1$ is acetyl, $R_2$ is COOMe, $R_3$ is Me).

Acetylation of the product of Example 1 with excess acetic anhydride in pyridine at 25° (24 hr.) gave, after workup and recrystallization from isopropanol, pure I ($R_1$ is acetyl, $R_2$ is COOMe, $R_3$ is Me) (83%), mp 147°–9°; $M^+$ = 418; ir (KBr) 1720, 1660 and 1600 cm$^{-1}$; uv $\lambda_{max}^{EtOH}$ = 275 ($\epsilon$ = 930), 225 ($\epsilon$ = 5900, shoulder) and 210 nm ($\epsilon$ = 16,500) nmr (DCCl$_3$) $\delta$ 2.09 (dd, 1H, J = 18.0 and 11.0 Hz.), 2.26 (s, 3H C$\underline{H}_3$CO), 2.32 (s, 3H, C$\underline{H}_3$CO), 2.30–2.67 (m, 3H), 2.71–2.88 (m, 2H), 3.05–3.14 (m, 2H), 3.50–3.66 (m, 1H), 3.74 (s, 3H, C$\underline{H}_3$O), 3.88 (s, 3H, C$\underline{H}_3$O) and 6.97 (s, 1H, Ar$\underline{H}$).

EXAMPLE 3

Dimethyl Ether of I ($R_1$ and $R_3$ are Me, $R_2$ is COOMe).

A mixture of the product of Example 1 (300 mg, 0.9 mmol), anhydrous K$_2$CO$_3$ (1.0 g, 7.24 mmol), Me$_2$SO$_4$ (504 mg, 4.0 mmol) and dry acetone (25 ml) was heated under reflux and stirred for 3.5 hr. The inorganic material was filtered off and washed with acetone. The filtrate was evaporated. The residue was dissolved in HCCl$_3$ (30 ml) and the solution washed with water, dried and evaporated to give the title compound (334 mg, 100%) mp 175°–177°. Recrystallization from isopropanol gave pure title compound, mp 176°–178°. $M^+$ = 362; ir (HCCl$_3$) 1736, 1718 (shoulder) and 1600 cm$^{-1}$; uv $\lambda_{max}^{EtOH}$ = 286 ($\epsilon$ = 3400), 250 ($\epsilon$ = 5150, shoulder) 213 nm ($\epsilon$ = 16,500); nmr (DCCl$_3$), $\delta$ 1.76–2.02 (1H, 5 lines), 2.21 and 2.34 (1H, 2 lines), 2.45–2.80 (3H, complex) 2.86–3.02 (3H, complex), 3.59–3.70 (1H, complex), 3.73 (s, 3H, OC$\underline{H}_3$), 3.84 (s, 3H, OC$\underline{H}_3$), 3.85 (s, 3H, OC$\underline{H}_3$) 3.89 (s, 3H, OC$\underline{H}_3$) and 6.39 (s, 1H, Ar$\underline{H}$).

EXAMPLE 4

Alkaline hydrolysis of I ($R_1$ is H, $R_2$ is COOMe, $R_3$ is Me) and decarboxylation to I ($R_1$, $R_2$, and $R_3$ are H).

To a refluxing solution of NaOH (3.0 g, 75 mmole) in H$_2$O (30 ml) which had been purged with N$_2$ for 0.5 hr, was added the product of Example 1 (2.5 g, 7.48 mmole). Refluxing under N$_2$ was continued 2.5 hr, after which the solution was cooled to 50° and acidified to pH 1.0 with 37% HCl. CO$_2$ was evolved. After cooling to 5°, the solution was filtered and the solid washed with H$_2$O and dried in air to give the monohydrate of I ($R_1$, $R_2$, and $R_3$ are H), mp 277°–78° dec.

Recrystallization was carried out by dissolving the solid in the minimum amount of 95% EtOH, treating with decolorizing charcoal, filtering, and adding two volumes of H$_2$O. Air-drying gave pure I ($R_1$, $R_2$ and $R_3$ are H), mp 282°–4°; $M^+$ = 262, ir (KBr) 3255, 1735, 1710, 1615, and 1600 cm$^{-1}$; uv, $\lambda_{max}^{EtOH}$ = 280 ($\epsilon$ = 2200), 223 ($\epsilon$ = 8500, shoulder), and 210 nm ($\epsilon$ = 14,000). The nmr spectrum (acetone-d$_6$) of a sample that had been dried in high vacuum overnight (100°) showed absorptions at $\delta$ 1.95 (dd, 1H, J = 17.0 and 11.0 Hz.), 2.18–3.05 (m, 7H), 3.52–3.82 (m, 1H), 5.55 (s, broad, 1H), 6.18 and 6.30 (AB system, $J_{AB}$ = 2.3 Hz, meta Ar$\underline{H}$), and 8.46 (s, broad, 2H).

EXAMPLE 5

Methylation of I ($R_1$, $R_2$, $R_3$ are H) to I ($R_1$ and $R_3$ are Me, $R_2$ is H).

To a solution of dimethyl sulfate (1.52 g, 12.0 mmole) in acetone (20 ml) was added the product of Example 4 (800 mg, 3.05 mmole) and anhydrous K$_2$CO$_3$ (1.66 g, 12.0 mmole). The solution was refluxed during five hours with stirring, cooled, filtered and evaporated.

Two recrystallizations from isopropanol gave pure material, mp 107°-9°; $M^+ = 304$; ir (HCCl$_3$) 1740, 1730, 1610 and 1590 cm$^{-1}$; uv $\lambda_{max}^{EtOH} = 280$ ($\epsilon = 2100$), 224 ($\epsilon = 8460$, shoulder) and 209 nm ($\epsilon = 14,300$); nmr (DCCl$_3$) $\delta$ 1.91 (dd, 1H, J = 17.5 and 12.0 Hz), 2.29 (d, 1H, J = 17.5 Hz), 2.45–3.07 (m, 6H), 3.50–3.68 (m, 1H), 3.75 (s, 3H, OC$\underline{H}_3$), 3.78 (s, 6H, 2 OC$\underline{H}_3$), 6.26 and 6.32 (AB system, $J_{AB} = 2.4$ Hz, meta Ar$\underline{H}$).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes of the invention and adapt it to various usages and conditions.

We claim:

1. A hexacarbomethoxy compound of the formula

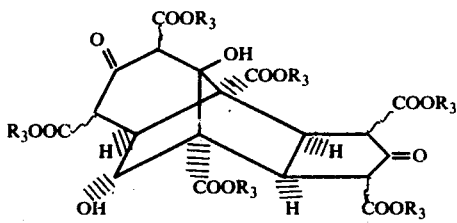

wherein R$_3$ is methyl.

* * * * *